(12) United States Patent
Kempkes et al.

(10) Patent No.: US 9,029,108 B2
(45) Date of Patent: May 12, 2015

(54) PULSED ELECTRIC FIELD (PEF) METHOD FOR CONTINUOUS ENHANCED EXTRACTION OF OIL AND LIPIDS FROM SMALL AQUATIC PLANTS

(75) Inventors: Michael Alan Kempkes, Westford, MA (US); Ian Roth, Westford, MA (US); Marcel Pierre Joseph Gaudreau, Lexington, MA (US)

(73) Assignee: Diversified Technologies, Inc., Bedford, MA (US)

( * ) Notice: Subject to any disclaimer, the term of this patent is extended or adjusted under 35 U.S.C. 154(b) by 774 days.

(21) Appl. No.: 12/807,857

(22) Filed: Sep. 15, 2010

(65) Prior Publication Data

US 2011/0107655 A1    May 12, 2011

Related U.S. Application Data (60) Provisional application No. 61/280,652, filed on Nov. 6, 2009.

(51) Int. Cl.
| | | |
|---|---|---|
| *C12N 13/00* | (2006.01) | |
| *C12P 1/02* | (2006.01) | |
| *C12P 7/64* | (2006.01) | |
| *C12N 1/06* | (2006.01) | |
| *C11B 1/10* | (2006.01) | |
| *C11B 3/00* | (2006.01) | |

(52) U.S. Cl.
CPC . *C12N 1/066* (2013.01); *C11B 1/10* (2013.01); *C11B 3/005* (2013.01); *C12N 13/00* (2013.01); *C12P 7/64* (2013.01)

(58) Field of Classification Search
CPC .......... A23C 3/0335; A23C 3/00; A23L 2/48; A23L 3/22; A23L 3/32; A23L 3/005; C02F 1/46; C02F 1/4608; C02F 2201/46175; C02F 1/48; C02F 2303/04; C11B 1/10; C11B 3/005; C12N 1/066; C12N 13/00; Y10S 99/14
See application file for complete search history.

(56) References Cited

U.S. PATENT DOCUMENTS

| | | | |
|---|---|---|---|
| 4,695,472 A | 9/1987 | Dunn et al. | |
| 5,690,978 A | 11/1997 | Yin et al. | |
| 5,776,529 A | 7/1998 | Qin et al. | |
| 7,507,341 B2 | 3/2009 | Gallagher et al. | |
| 2004/0084381 A1 | 5/2004 | Korenev | |
| 2005/0026202 A1 | 2/2005 | Edman et al. | |
| 2007/0207528 A1 | 9/2007 | Picataggio et al. | |
| 2009/0035856 A1 | 2/2009 | Galliher et al. | |
| 2009/0087900 A1 | 4/2009 | Davey et al. | |
| 2011/0095225 A1 | 4/2011 | Eckelberry et al. | |

FOREIGN PATENT DOCUMENTS

| | | | |
|---|---|---|---|
| CA | 2755040 A1 | 9/2010 | |
| WO | WO 2008/098298 A1 | 8/2008 | |

OTHER PUBLICATIONS

"Pulsed Electric Field Processing"—Wikipedia, the free encyclopedia, Jan. 14, 2010, 1 pg. (unnumbered).
M. Sack et al., "Upgrade of the Electroporation Device KEA-MOBIL", Proceedings of the 2nd Euro-Asian Pulsed Power Conference, Vilnius, Lithuania, Sep. 22-26, 2008, vol. 115 (2009), No. 6, pp. 1081-1083.
Eltron Research & Development Tech Brief, "Electroporation of Algae Cells", www.eltronresearch.com Nov. 2009, 1 pg.
Robert Henrikson, AlgaeAlliance.com, Real World Experiences in Growing Algae, What happened over the past 30 years growing and marketing algae and what are the lessons for today?, Algae World Summit 2010 Symposium, May 17, 2010, San Diego, CA, 46 pgs.
M. Sack et al., "Research on Industrial-Scale Electroporation Devices at Forschungszentrum Karlsruhe and Cooperation Partners", BFE 2009, Compiègne, France, Oct. 2009, pp. 265-270.
Written Opinion from the International Searching Authority, International Application No. PCT/US2010/002899, Jan. 11, 2011, 5 pgs. (unnumbered).
Liu et al., "Nickel-inducible lysis system in *Synechocystis* sp. PCC 6803", PNAS, vol. 106, No. 51, Dec. 22, 2009, p. 21550-21554.
"Poking Holes in Corn for Ethanol", http://newenergyandfuel.com/ http:/newenergyandfuel/com/2009/02/12/poking-holes-in-corn-for-ethanol/, 2 pgs., 2009.
Cravotto G. et al. "Improved extraction of vegetable oils under high-intensity ultrasound and/or microwaves", Ultrasonics: Sonochemistry, Butterworth-Heinemann, GB, vol. 15, No. 5, Jul. 1, 2008, pp. 898-902.
Monica Heger, "A new processing scheme for algae biofuels", MIT Technology Review, May 1, 2009, XP002713605, 1 pg.
Guderjan, M. et al., "Impact of pulsed electric field treatment on the recovery and quality of plant oils", Journal of Food Engineering, Barking, Essex, GB, vol. 67, No. 3, Apr. 1, 2005, pp. 281-287.

*Primary Examiner* — Debbie K Ware
(74) *Attorney, Agent, or Firm* — Iandiorio Teska & Coleman, LLP (57) ABSTRACT

A pulsed electric field method for the continuous extraction of oil and lipids from small aquatic plants, the method including providing a continuous flow of a slurry of small aquatic plants. A continuous flow of small aquatic plants is directed to a treatment zone. Pulsed electric fields are applied to the treatment zone to lyse cell walls of the small aquatic plants to enhance extraction of oil and lipids therefrom.

16 Claims, 6 Drawing Sheets

PULSED ELECTRIC FIELD (PEF) METHOD FOR CONTINUOUS ENHANCED EXTRACTION OF OIL AND LIPIDS FROM SMALL AQUATIC PLANTS

RELATED APPLICATIONS

This application hereby claims the benefit of and priority to U.S. Provisional Application Ser. No. 61/280,652, filed on Nov. 6, 2009 under 35 U.S.C. §§119, 120, 363, 365, and 37 C.F.R. §1.55 and §1.78, which is hereby incorporated herein by reference.

FIELD OF THE INVENTION

This invention relates to a pulsed electric field (PEF) method for the continuous enhanced extraction of oil and lipids from small aquatic plants for use in the production of a biofuel.

BACKGROUND OF THE INVENTION

Biofuels, such as ethanol, biodiesel, and the like, show promise as an abundant source of renewable energy, but only if they can be produced at competitive prices. Some conventional methods for the production of biofuels may use high sugar feedstocks, such as corn, sugar cane, and the like. Because these feedstocks are also consumed by humans and livestock, using such materials for the production of biofuels may result in a shortage of supply which can increases the cost of the biofuel.

In order to create a biofuel from feedstock, one key step in the process requires the breaking down, or lysis, of the cell walls of the feedstock to release the carbohydrates, oil, lipids, and other compounds stored therein which is then processed downstream by enzymatic treatment to create a biofuel. Conventional methods to perform cell lysis on feedstock often rely on acids and steam which are dangerous and expensive.

Another conventional method for the production of a commonly known biofuel, ethanol, typically uses feedstock, such as sugarcane, or starch from corn. Producing ethanol from sugar or starch is well known but requires feedstock as the raw materials. Ethanol may also be produced from non-feedstock materials, often referred to as cellulosic material, e.g., corn stover or switch grass. Producing ethanol from cellulosic materials typically relies on pre-treating the cellulosic material to remove the lignin sheath from the cells which makes the cellulose, or carbohydrate, therein assessable. The cellulose is then broken down into its component sugars through hydrolysis and the resulting sugars are fermented to make ethanol. Such a technique is expensive, and cumbersome.

Biofuels may also be produced from small aquatic plants, such as algae or phytoplankton. Small aquatic plants store oil and lipids inside that cells which can be used to produce biofuels. However, liberating the oil and lipids from small aquatic plants in a cost-effective, continuous, manner is quite difficult. One conventional process for the extraction of oil and lipids from algae relies on drying the algae and extracting the oil and lipids using hexane or supercritical fluid $CO_2$. Such a technique is expensive, difficult to perform in a continuous flow process, and uses dangerous and toxic materials.

PEF treatment is a process which uses short, high voltage pulses of electricity and a specialized treatment chamber to disrupt cell membranes in a process called electroporation. See e.g., U.S. Pat. No. 5,690,978 entitled "High Voltage Pulsed Electric Field Treatment Chamber For The Preservation Of Liquid Food Products", incorporated by reference herein. As disclosed therein, PEF is used to expand and rupture pores in the cell membrane of bacteria or microorganisms to kill them and preserve liquid food products.

However, to date, PEF has not been used for continuous enhanced extraction of oil and lipids, as well as other valuable compounds from small aquatic plants to produce a biofuel.

BRIEF SUMMARY OF THE INVENTION

This invention features a pulsed electric field method for the continuous extraction of oil and lipids from small aquatic plants, the method including providing a continuous flow of a slurry of small aquatic plants. A continuous flow of small aquatic plants is directed to a treatment zone. Pulsed electric fields are applied to the treatment zone to lyse cell walls of the small aquatic plants to enhance extraction of oil and lipids, therefrom.

In one embodiment, the method may include the step of applying pulsed electric fields having a magnitude greater than at least 1 kV/cm. The method may include the step of applying pulsed electric fields having a magnitude in the range of about 5 keV/cm to about 30 keV/cm. The method may include the step of applying pulsed electric fields having a magnitude chosen to optimize lysing of the cell walls of the small aquatic plants. The method may include the step of applying the pulsed electric fields having an optimized magnitude and an optimized pulsed width. The method may include the step of applying pulsed magnetic fields having a magnitude in the range of about 20 kV/cm to about 30 kV/cm and a pulse width in the range of about 1 μs to about 10 μs. The method may include the step of applying pulsed electric fields chosen to optimize energy consumption needed to lyse the cells walls of the small aquatic plants. The method may include the step of providing the continuous flow of slurry of small aquatic plants at a flow rate of at least 1 l/h. The method may include the step of providing the continuous flow of the slurry of small aquatic plants at a flow rate of about 10 l/h to about 100,000 l/h. The method may include the step of measuring the flow rate of the slurry of small aquatic plants. The method may include the step of adjusting the frequency of the pulsed electric fields in proportion to the measured flow rate. The small aquatic plants may include algae or phytoplankton. The method may include the step of using the oil and lipids extracted from the small aquatic plants for the production of biofuel. The method may include the step of applying pulsed electric fields to the treatment zone to lyse cell walls of the small aquatic plants to enhance extraction of other compounds. The method may include the step of applying pulsed electric fields to the treatment zone to lyse cell walls of the small aquatic plants to enhance extraction of one or more of: EPA oil, DHA oil, antioxidants, stabilizers, omega 3 oil, pigments, food colorings, and food ingredients.

This invention also features a pulsed electric field method for the continuous extraction of oil, lipids and/or other compounds from small aquatic plants, the method including: providing a continuous flow of a slurry of small aquatic plants. A continuous flow of small aquatic plants is directed to a treatment zone. Pulsed electric fields are applied to the treatment zone to lyse cell walls of the small aquatic plants to enhance extraction of oil, lipids and/or other compounds therefrom.

BRIEF DESCRIPTION OF THE SEVERAL VIEWS OF THE DRAWINGS

Other objects, features and advantages will occur to those skilled in the art from the following description of a preferred embodiment and the accompanying drawings, in which.

DETAILED DESCRIPTION OF THE INVENTION

Aside from the preferred embodiment or embodiments disclosed below, this invention is capable of other embodiments and of being practiced or being carried out in various ways. Thus, it is to be understood that the invention is not limited in its application to the details of construction and the arrangements of components set forth in the following description or illustrated in the drawings. If only one embodiment is described herein, the claims hereof are not to be limited to that embodiment. Moreover, the claims hereof are not to be read restrictively unless there is clear and convincing evidence manifesting a certain exclusion, restriction, or disclaimer.

Figure 1:
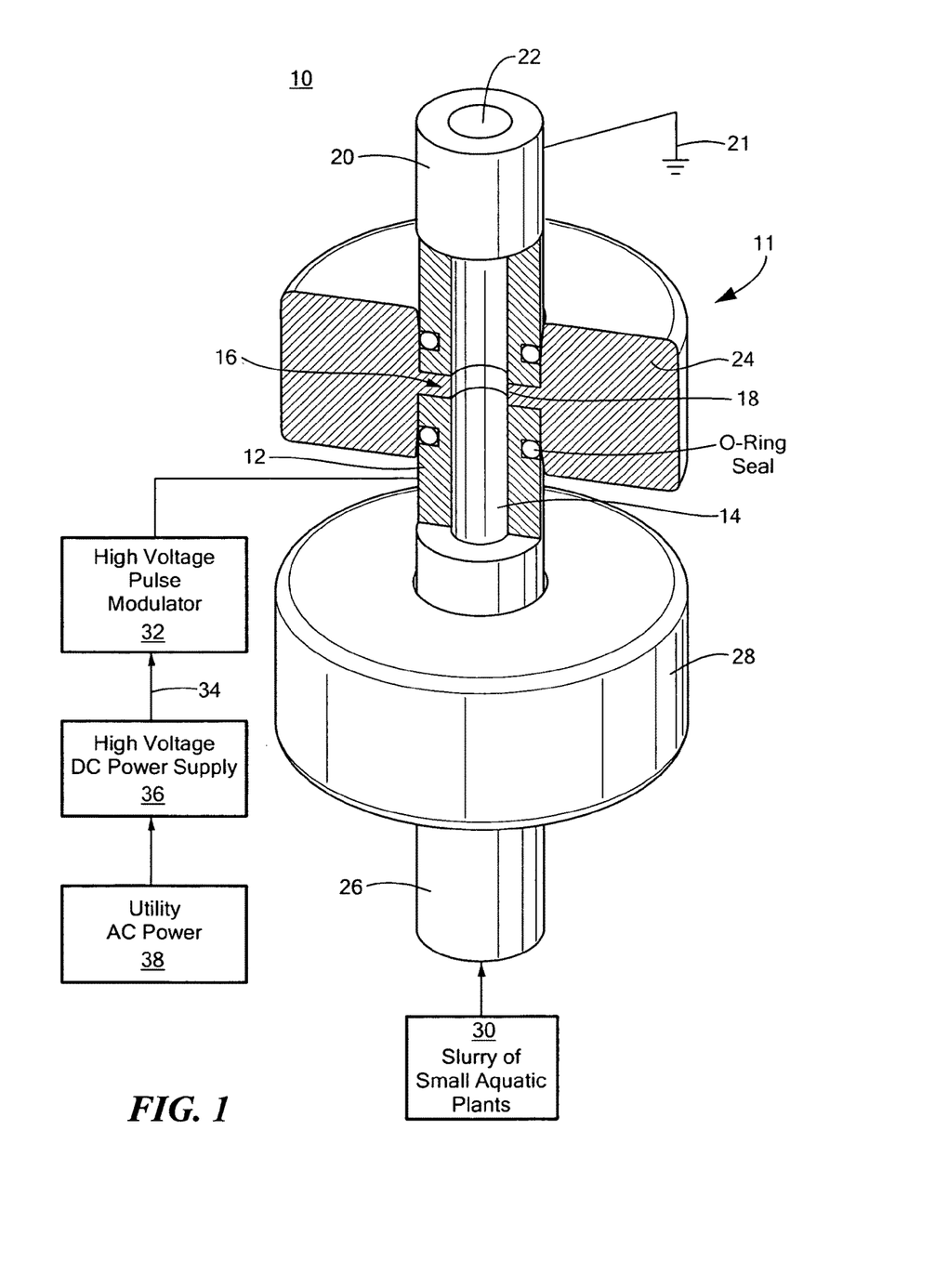
FIG. 1 is a schematic front-view of one embodiment of the primary components used for the method of continuous extraction of oil and lipids from small aquatic plants of this invention.

There is shown in FIG. 1, one embodiment of pulsed electric field (PEF) system 10 used for one embodiment of the method of continuous extraction of oil and lipids from small aquatic plants of this invention. As shown is a cutaway view of one-half of PEF treatment chamber 11 of PEF system 10 which, in this example, includes high voltage electrode 12 with channel 14, treatment zone 16 with channel 18, ground electrode 20 with outlet 22 and insulator 24 between high voltage electrode 12 and ground electrode 20. High voltage electrode 12 is in communication with high voltage pulse modulator 32. High voltage pulse modulator 32 preferably receives high voltage DC by line 34 from high voltage DC supply 36 coupled to utility AC power 38. Ground electrode 20 is connected to ground 21. Additional details of the structure and operation of chamber 11 are disclosed in U.S. Pat. No. 5,690,978, cited supra, incorporated by reference herein.

The other half of PEF treatment chamber 11 preferably includes at least another treatment zone (not shown) located between ground electrode 26, insulator 28 and high voltage electrode 12, each having a similar structure and connection to high voltage pulse modulator 32 as discussed above. Single high voltage electrode 12 faces two grounded electrodes 22, 26 (one on each side), producing two areas with electric fields. In one design, system 10 includes two PEF treatment chambers each having two treatment zones therein, e.g., PEF treatment chambers 11 and 13, FIG. 2, discussed in further detail below. System 10 may include one or more treatment chambers.

One example of the method of continuous extraction of oil and lipids from small aquatic plants of this invention is now discussed with reference to the cutaway section of chamber 11, FIG. 1. The other half of chamber 11, as well as chamber 13, FIG. 2, operate in a similar manner.

In this exemplary operation, slurry of small aquatic plants 30, e.g., algae, phytoplankton, or similar type small aquatic plants, is continuously fed into channel 14 of high voltage electrode 12. The continuous flow rate of slurry of small aquatic plants 30 fed into channel 14 is preferably at least 1 liter per hour (l/h). In other examples, the continuous flow rate of slurry of small aquatic plants 30 into channel 14 may be in the range of about 10 l/h to over 100,000 l/h.

Figure 3A:
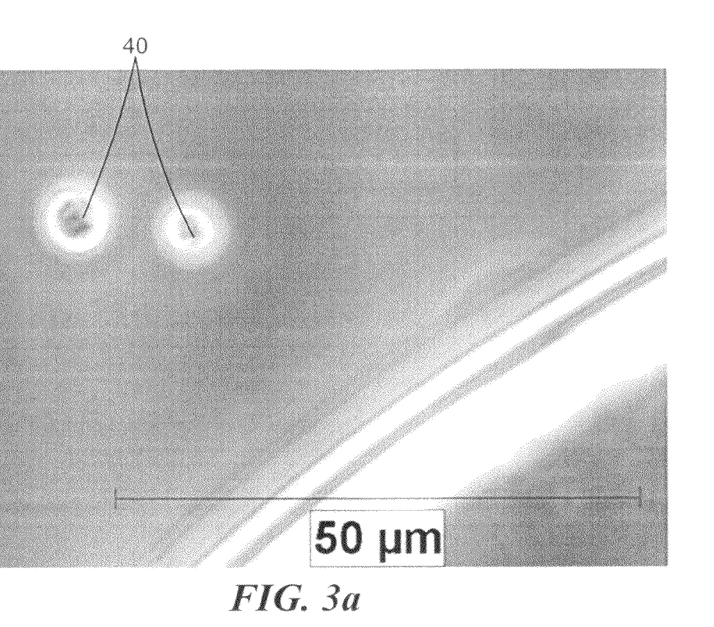
FIGS. 3A and 3B are microscopic photographs showing the cell walls of small aquatic plants before and after being exposed to PEFs in accordance with one embodiment of the method of this invention.
Figure 3B:
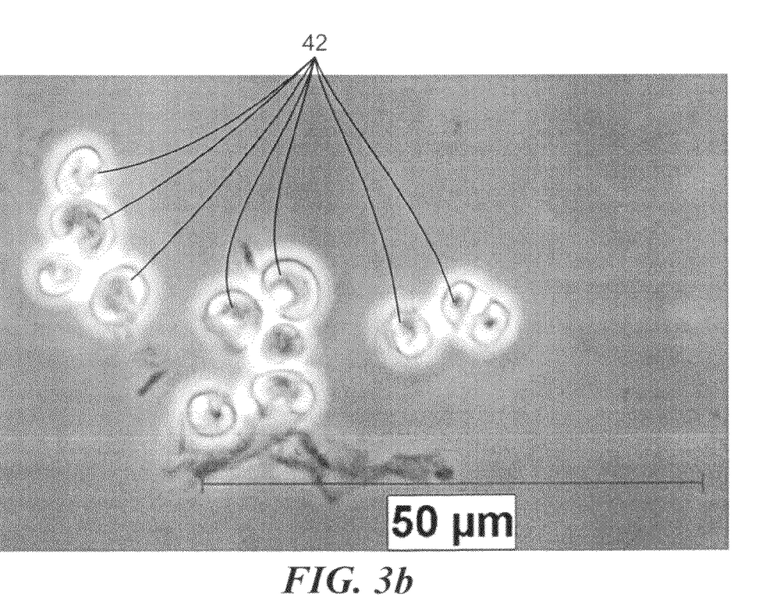

High voltage pulsed signals generated by high voltage pulse modulator 32 are applied to high voltage electrode 12 to create an electric field in treatment zone 16. Due to the physical configuration of high voltage electrode 12, ground electrode 20, and insulator 24, a nearly uniform electric field will be present in treatment zone 18. The electric field in treatment zone 16 will have a vector direction pointing from high voltage electrode 16 to ground electrode 20. Therefore, as the continuous flow of slurry of small aquatic plants 30 passes through channel 14 in high voltage electrode 12, to channel 18 in treatment zone 16, and then to outlet 22 in ground electrode 20, slurry of small aquatic plants 30 is subject to an applied electric field that is concentrated in treatment zone 16. This causes the cell walls of small aquatic plants to lyse and release the oil and lipids as well as other valuable compounds therein. The other valuable compounds released may include EPA oil, DHA oil, antioxidants, stabilizers, omega 3 oil, pigments, food colorings, food ingredients, such as alginates, agar, carrageenan, diatomeaceus earth, and the like, or any other similar type compounds. The solution of lysed cells, partially lysed cells, unlysed cells, and oil and lipids, and other compounds exits via port 22 for additional processing to create a biofuel and other products. The remaining processes of extraction and refinement are conventional and are not discussed here. FIG. 3A shows one example of small aquatic cells 40 before being lysed and FIG. 3B shows one example of small aquatic cells 42 which have effectively been lysed to release the oil and lipids therein, in accordance with one embodiment of the method of this invention.

The pulsed electric fields in treatment zone 16, FIG. 1, expand existing pores within the cell walls of the small aquatic plants until they rupture, or lyse, opening the cells to the surrounding solution through electroporation. This is believed to occur due to migration of ions towards the membrane of the cells, causing an enhanced electric field to cross the membrane resulting in growth of pores in the cell walls. The PEF treatment protocol may be defined by two parameters: the magnitude of the electric field strength (V/cm) and the total treatment time required for each element of the slurry of small aquatic plants 30. It is believed that there is a critical electric field, $E_{CRIT}$, that needs to be exceeded for a given total time in order for electroporation to reliably occur across a population of cells of the slurry of small aquatic plants 30. $E_{CRIT}$ is thought to be directly related to the size of the cells to be electroporated, represented by the ratio of the cell wall thickness to the diameter of the cell. Small cells, such as bacteria, require higher field strengths than plant cells, since this ratio is higher. Small aquatic plants, e.g., algae, phytoplankton, and the like, are between the two sizes. A typical treatment protocol for the extraction of oil and lipids from small aquatic plants may require about 5 kV/cm pulsed electric fields for as little as 5 μs to yield optimum enhancement of the release of oil and lipids from the cells of the small aquatic plants. In other examples, the magnitude of the pulsed electric fields may be in the range of about 5 kV/cm to about 40 kV/cm. Thus, the magnitude of the pulsed electric fields is preferably chosen to optimize lysing of the cell walls of the small aquatic plants with the lowest energy applied.

In other examples, the magnitude of the pulse electric fields may be in the range of about 20 kV/cm to about 30 kV/cm and the pulse width may be in the range of about 1 μs to about 10 μs. The frequency of the pulse electric fields may be adjusted in proportion to the flow of the slurry of small aquatic plants 12 to achieve an applied energy of 10 to 300 kJ/liter, depending on the applied voltage, required treatment time, and conductivity of the slurry. The adjustment may be automatic.

Figure 4:
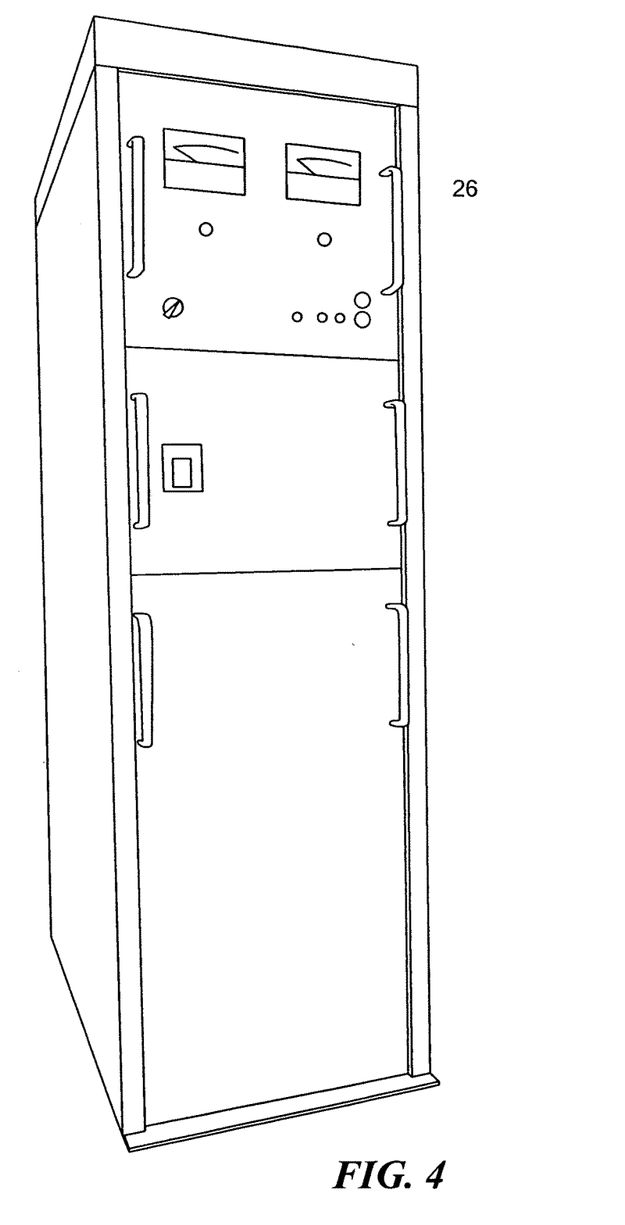
FIG. 4 is a three-dimensional front-view of one embodiment of the high voltage DC power supply shown in FIG. 1.

As discussed above, there are few key devices used by the method of continuous extraction of oil and lipids from small aquatic plants of this invention. One includes high voltage DC power supply 36, FIG. 1, which converts utility AC power 38 into high voltage DC. In one example, high voltage power supply 36 is a high frequency switching supply. In this design, input utility AC power 38 is preferably rectified and "chopped" at high frequencies, e.g., about 10 to about 50 kHz, then passed to a transformer rectifier. DC power supply 36 may provide highly regulated and rapidly adjustable output voltage which supports tight control of the PEF process parameters. In one example, DC power supply 36 may used in applications of approximately 500 kW, which supports PEF processing at flow rates up to 100,000 l/hr. FIG. 4 shows one example of high voltage DC power supply 26 available from the assignee hereof, Diversified Technologies, Inc. (Bedford, Mass.). Other methods for creating high voltage DC power are known to those skilled in the art.

Figure 5:
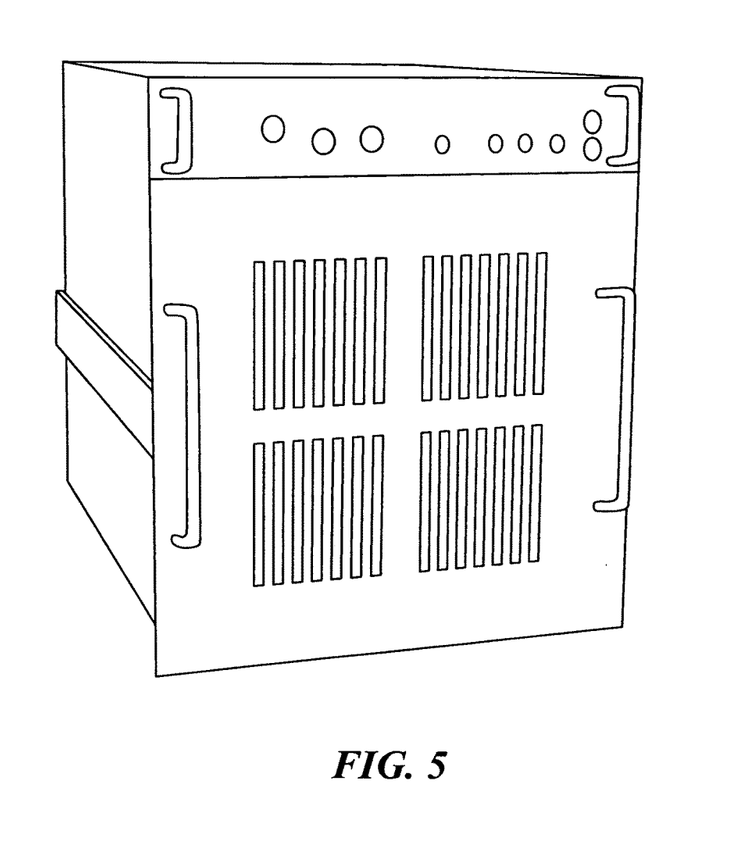
FIG. 5 is a three-dimensional front-view of one embodiment of the high voltage pulse modulator shown in FIG. 1.

Another key device used by the method for the continuous extraction from oil, lipids, and/or other compounds from small aquatic plants of one embodiment of this invention is high voltage pulse modulator 32, FIG. 1, which transforms the average power output by high voltage DC power supply 36 into short, high-power pulses. Preferably, high voltage pulse modulator 32 uses a "hard switch" which can directly switch full voltage. High voltage pulse modulator 32 also preferably has a low impedance to provide consistent output voltage over a range of peak currents required as the fluid conductivity of slurry of small aquatic plants 30 varies. Solid state switches are ideally suited for both of these requirements which can be obtained from the assignee hereof, Diversified Technologies, Inc. (Bedford, Mass.). High voltage pulse modulator is preferably a solid-state, high-voltage modulator, e.g., as disclosed in U.S. Pat. Nos. 5,440,610 and 6,900,557, by the assignee hereof, Diversified Technologies, Inc. (Bedford, Mass.), incorporated by reference herein. FIG. 5 shows one example of high voltage pulse modulator 32 available from Diversified Technologies, Inc. (Bedford, Mass.). While this represents one method, many other types of pulse modulators are known in the art and may be used.

Figure 2:
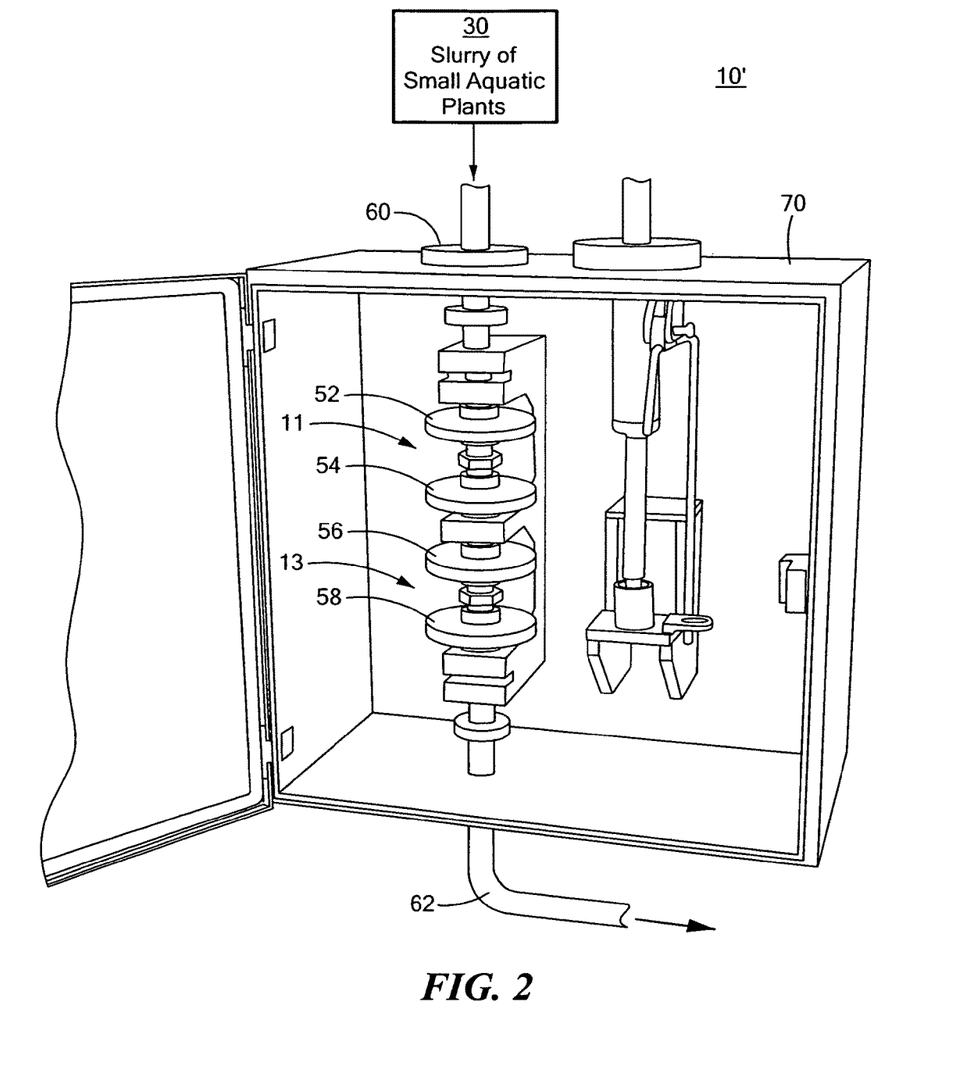
FIG. 2 is a three-dimensional view of one embodiment of the system shown in FIG. 1 including a plurality of treatment chambers.
Figure 6:
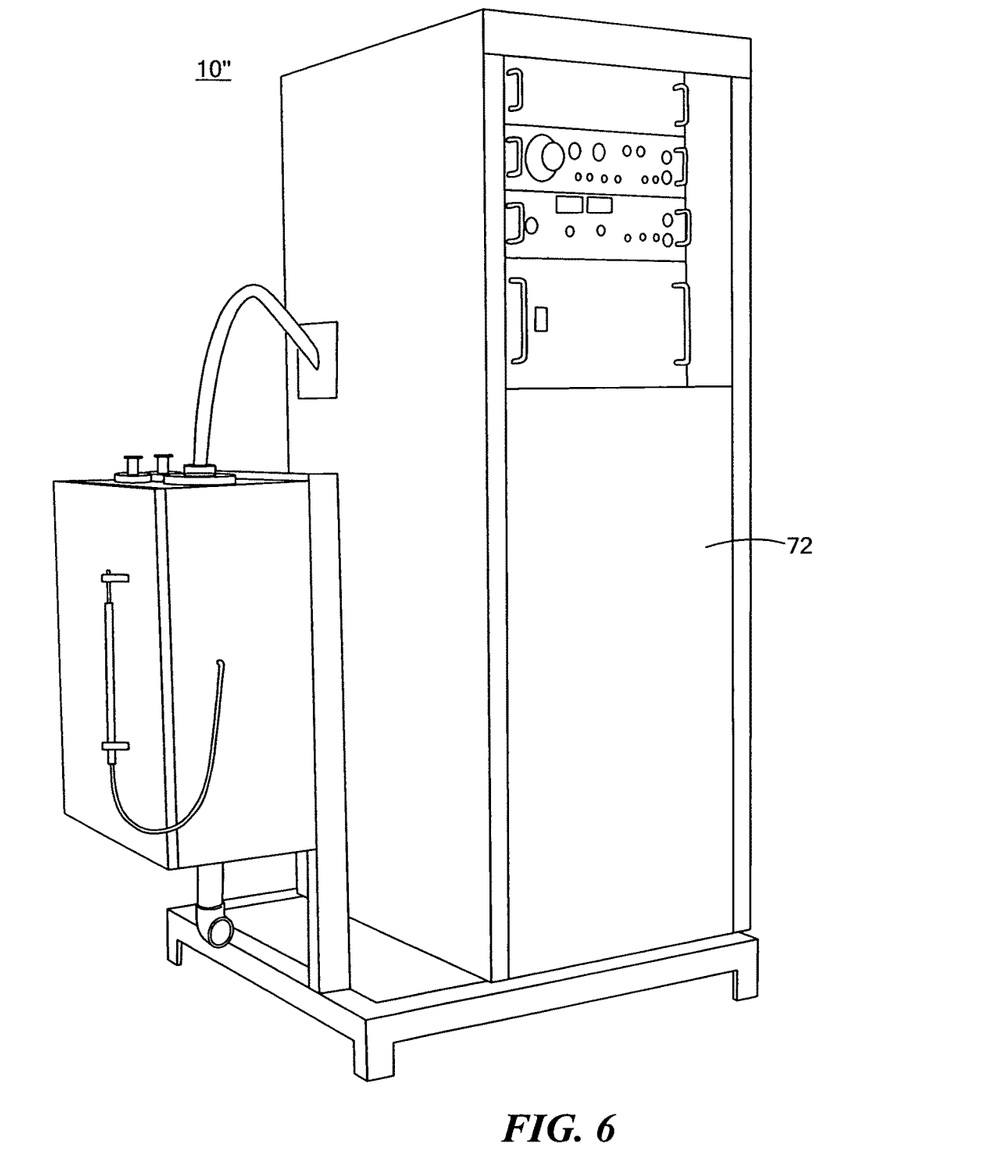
FIG. 6 is a three-dimensional view of one embodiment of a PEF treatment system utilized in accordance with the method for the continuous extraction of oil and lipids from small aquatic plants of this invention.

In one design, the method of continuous extraction of oil, lipids, and/or other compounds from small aquatic plants of this invention utilizes PEF treatment system 10', FIG. 2, discussed above, which includes a plurality of treatment chambers 11 and 13 each having corresponding high voltage electrodes and ground electrodes which are coupled to high voltage pulse modulator 32, FIG. 1, and a high voltage DC power supply 36. The insulators between the high voltage electrodes and ground electrodes are shown at 52, 54, 56, and 58. In this example, chambers 11 and 13, FIG. 2, are housed in housing 70. Chambers 11 and 13 provide four treatment zones. Slurry of small aquatic plants 30 enters at inlet 60 and the processed solution which includes the oil, lipids, and/or other compounds extracted from slurry of small aquatic plants 30 exits via outlet 62. PEF treatment system 10' may be used for one embodiment of the method of this invention. In one example, housing 70, FIG. 2, with treatment chambers 11 and 13 is connected to cabinet 72, FIG. 6, with high voltage pulse modulator 24 and high voltage DC power supply 26 therein.

In accordance with one embodiment of the method of this invention, the magnitude of the pulsed electric fields needed to lyse the cell walls of small aquatic plants of a predetermined size are preferably chosen to minimize energy consumption while achieving the desired level of lysing of the cells in the slurry.

The cost of PEF processing is typically dominated by the electrical energy required which depends on the square of the electric field. Therefore, there may be a significant cost benefit for the method described herein to operate at the lowest practical field. In general, the electric field required is inversely proportional to the cell size of the small aquatic plants. The electric field to electroporate plant cells is relatively low, e.g., about 1-5 keV/cm, compared to that of a bacterium, e.g., about 30-35 keV. The field required for enhancing the extraction of oil and lipids from small aquatic plants such as algae and phytoplankton is about 5 kV/cm to about 20 kV/cm, but may be as high as 40 kV/cm for some species.

The fluid conductivity of slurry of small aquatic plants 30, FIGS. 1 and 2, determines how much current flows through slurry 30 when the pulse electric fields are applied to treatment zone 18. This mandates how much energy will be used in applying the pulsed electric fields. Conductivity is a function of ions contained in the slurry of small aquatic plants. The energy volume, w, deposited in the slurry of aquatic plants 30 treated by PEF may be given by the formula:

$$w = \sigma E^2 t \quad (1)$$

where σ is the conductivity of the slurry of small aquatic plants, E is the electric field, and t is the total treatment time. We can convert this to the cost, c, using the equation:

$$c = wR/(fY) = \sigma E^2 t R/(fY) \quad (2)$$

where R is the cost per joule of the electricity and equipment, f is the fraction of the material in the slurry, and Y is the yield or the volume of fuel per volume of material.

Preferably, the electric field should be minimized, since the cost depends on the square of the electric field. For the PEF method hereof, there appears to be a threshold electric field, $E_{CRIT}$, discussed above. Below $E_{CRIT}$, cells are not electroporated, independent of the pulse duration. Above $E_{CRIT}$, the total energy, which scales as the square of the field strength, and directly with treatment time, is preferably minimized. The conductivity of the slurry is also preferably minimized. As an example, treating algae in sea water is more costly because the sea water raises the conductivity and requires more power. Washing the algal biomass to reduce salinity may be required to minimize overall costs. In one example, the slurry of small aquatic plants 30 is preferably concentrated (low water content) to reduce the total volume that must be PEF processed.

The electrical cost, R, in equation (2) above, depends on the cost of the electricity and the PEF devices discussed above with reference to FIGS. 1-6. One estimate for cost, c, of R is about $2.7 \times 10^{-8}$ \$/J. One estimate for the cost of the electricity about 8 ¢/kW-hr (a nominal national average), which is about $2.2 \times 10^{-8}$ \$/J. The cost to operate is about 1 \$/W for the modulator that produces the switched pulses, and about 0.2 \$/W for the power supply that produces the high voltage DC from the AC input. The cost of the treatment chambers is very low in comparison, and is not considered here. These costs are converted to dollars per joule assuming the devices will be in service for 10 years ($3.2 \times 10^8$ s), at 80% utilization:

$$R_{equipment}=1.2\$/W/(3.2\times10^8 s\cdot 80\%)=4.7\times10^{-9}\$/J \quad (3)$$

The total cost is the sum of the electricity and equipment costs:

$$R=R_{electricity}+R_{equipment}=2.2\times10^{-8}+4.7\times10^{-9}=2.7\times10^{-8}\$/J \quad (4)$$

The electricity dominates the overall cost of the PEF method of this invention, since the equipment cost is only 18% of the total.

In one example, to extract oil and lipids from algae, or similar type small aquatic plants, the PEF method discussed herein is assumed to be applied to a concentrated algae solution. After harvesting and dewatering, the algae are preferably at a 50% concentration and the yield of oil and lipids from the wet algae is about 10-20%, depending on the species. A conservative electric field of 20 kV/cm and a treatment time of 10 µs is sufficient to electroporate the cells of the algae. In the optimum value of the electric field may be lower. The conductivity of the slurry of algae is about $\leq 10$ mS/cm, which is the conductivity of brackish water that algae can be grown in. It is possible that this number may be reduced, e.g., either by using algae or similar small aquatic plants grown in fresh water, or by rinsing the salt-water algae with fresh water. Using equation (1) above and a value of 0.01 S/cm for $\sigma$, 20 kV/cm for E, and 10 µs for t yields an energy requirement of about 40 J/cm$^3$, or 40 kJ/liter.

The cost for the energy requirement is calculated using the formula:

$$c=wR/(fY) \quad (5)$$

Using a value of 40 J/cm$^3$ for w, $2.7\times10^{-8}$ \$/J for R, 0.5 for f, and 0.08 for Y yields a cost of \$0.10/gal.

One example of the cost for conventional drying is as follows:

4.5 kW-hr/kg dry mass×1 kg dry mass./0.4 kg oil and lipids×3.35 kg oil and lipids/gal×4.8 ¢/kW-hr. This totals to about \$1.81/gal. Note that the energy cost used above is about 4.8 ¢/kW-hr instead of 8 ¢/kW-hr because the energy is from fuel instead of electricity. As can be seen, the cost of the PEF method for the continuous extraction of oil and lipids from small aquatic plants of one embodiment of this in invention is only about \$0.10/gal which is significantly lower than the \$1.81/gal of conventional methods. The result is the net savings in this example is about \$1.71/gallon.

Although specific features of the invention are shown in some drawings and not in others, this is for convenience only as each feature may be combined with any or all of the other features in accordance with the invention. The words "including", "comprising", "having", and "with" as used herein are to be interpreted broadly and comprehensively and are not limited to any physical interconnection. Moreover, any embodiments disclosed in the subject application are not to be taken as the only possible embodiments.

In addition, any amendment presented during the prosecution of the patent application for this patent is not a disclaimer of any claim element presented in the application as filed: those skilled in the art cannot reasonably be expected to draft a claim that would literally encompass all possible equivalents, many equivalents will be unforeseeable at the time of the amendment and are beyond a fair interpretation of what is to be surrendered (if anything), the rationale underlying the amendment may bear no more than a tangential relation to many equivalents, and/or there are many other reasons the applicant can not be expected to describe certain insubstantial substitutes for any claim element amended.

Other embodiments will occur to those skilled in the art and are within the following claims.

What is claimed is:

1. A pulsed electric field method for the continuous extraction of oil and lipids from small aquatic plants, the method comprising: providing a continuous flow of a slurry of small aquatic plants;
   directing continuous flow of small aquatic plants to a treatment zone; and
   applying pulsed electric fields with a high voltage electrode and a ground electrode both in contact with the continuous flow to the treatment zone to lyse cell walls of the small aquatic plants by electroporation to enhance extraction of oil and lipids therefrom.

2. The method of claim 1 further including the step of applying pulsed electric fields having a magnitude greater than at least 1 kV/cm.

3. The method of claim 2 further including the step of applying pulsed electric fields having a magnitude in the range of about 5 kV/cm to about 40 kV/cm.

4. The method of claim 1 further including the step of applying pulsed electric fields having a magnitude chosen to optimize lysing of the cell walls of the small aquatic plants.

5. The method of claim 1 further including the step of applying pulsed electric fields chosen to optimize energy consumption needed to lyse a percentage of the cells walls of the small aquatic plants.

6. The method of claim 1 further including the step of providing the continuous flow of slurry of small aquatic plants at a flow rate of at least 1 l/h.

7. The method of claim 6 further including the step of providing the continuous flow of the slurry of small aquatic plants at a flow rate of about 10 l/h to about 100,000 l/h.

8. The method of claim 1 further including the step of measuring the flow rate of the slurry of small aquatic plants.

9. The method of claim 8 further including the step of adjusting the frequency of the pulsed electric fields in proportion to the measured flow rate.

10. The method of claim 1 in which the small aquatic plants includes algae.

11. The method of claim 1 in which the small aquatic plants includes phytoplankton.

12. The method of claim 1 further including the step of producing a biofuel using the oil and lipids extracted from the small aquatic plants.

13. The method of claim 1 further including the step of applying pulsed electric fields to the treatment zone to lyse cell walls of the small aquatic plants to enhance extraction of one or more of: EPA oil, DHA oil, antioxidants, stabilizers, omega 3 oil, pigments, food colorings and food ingredients.

14. The method of claim 1 further including the step of applying the pulsed electric fields having an optimized magnitude and an optimized pulsed width.

15. The method of claim 14 further including the step of applying pulsed electric fields having a magnitude in the range of about 20 kV/cm to about 30 kV/cm and a pulse width in the range of about 1 µs to about 10 µs.

16. A pulsed electric field method for the continuous extraction of oil, lipids and other compounds from small aquatic plants, the method comprising:
   providing a continuous flow of a slurry of small aquatic plants;
   directing continuous flow of slurry of small aquatic plants to a treatment zone; and
   applying pulsed electric fields with a high voltage electrode and a ground electrode both in contact with the continuous flow to the treatment zone to lyse cell walls of the small aquatic plants by electroporation to enhance extraction of oil, lipids, and other compounds therefrom.

* * * * *